United States Patent [19]

Burdinski et al.

[11] Patent Number: 5,189,165
[45] Date of Patent: Feb. 23, 1993

[54] PROCESS FOR THE PREPARATION OF 1,1-DISUBSTITUTED CYCLOPROPANE DERIVATIVES

[75] Inventors: Gerhard Burdinski, Nastätten; Reinhard Kirsch, Frankfurt am Main; Hariolf Kottmann, Hofheim am Taunus, all of Fed. Rep. of Germany

[73] Assignee: Hoechst Aktiengesellschaft, Frankfurt am Main, Fed. Rep. of Germany

[21] Appl. No.: 631,399

[22] Filed: Dec. 21, 1990

[30] Foreign Application Priority Data

Dec. 23, 1989 [DE] Fed. Rep. of Germany ....... 3942946

[51] Int. Cl.$^5$ ................. C07D 239/02; C07C 331/00; C07C 319/12
[52] U.S. Cl. ................... 544/298; 544/3334; 544/335; 546/173; 546/174; 546/290; 546/301; 546/302; 548/160; 548/165; 548/187; 548/204; 548/225; 548/226; 548/236; 548/307.1; 548/306.7; 549/62; 549/66; 549/78; 549/473; 558/10; 558/44; 558/53; 558/57; 558/454; 568/42; 568/43
[58] Field of Search ...................... 558/10; 568/42, 43; 549/78, 473; 546/174, 173, 240, 301, 302; 548/170, 187, 204, 330, 160, 165, 225, 226, 236, 325, 329; 544/335, 334, 298

[56] References Cited

U.S. PATENT DOCUMENTS 4,514,418  4/1985  Saito et al. ............................ 558/10

FOREIGN PATENT DOCUMENTS 0237917  9/1987  European Pat. Off. .

*Primary Examiner*—C. Warren Ivy
*Assistant Examiner*—Raymond Covington
*Attorney, Agent, or Firm*—Finnegan, Henderson, Farabow, Garrett and Dunner

[57] ABSTRACT

A process for preparing a compound I

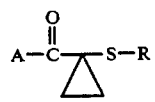

(I)

with
A = t-butyl, aryl and
R = alkyl, alkenyl, alkynyl, alkenynyl, cycloalkyl(alkyl), aryl, arylalkyl, alkyl-S-(-O)-aryl by reacting a compound III

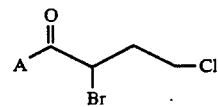

(III)

with a compound IV

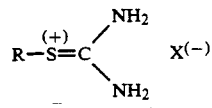

(IV)

under the conditions of a phase-transfer reaction, is described. The process gives excellent yields and is not associated with the unpleasant odor of mercaptans.

3 Claims, No Drawings

PROCESS FOR THE PREPARATION OF 1,1-DISUBSTITUTED CYCLOPROPANE DERIVATIVES

The invention relates to a process for the preparation of 1,1-disubstituted cyclopropane derivatives which have a substituent bonded via a sulfur atom on the cyclopropyl ring. The compounds synthesized by the process according to the invention are precursors for highly effective pharmaceuticals, especially antimycotics, and crop protection agents, for example fungicides and growth regulators.

European Published Specification 0 237 917 (Patent Application EP 87103391.6) describes compounds of the structure I

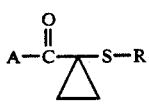

as intermediates for the synthesis of derivatives of the structure II

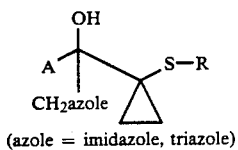

(azole = imidazole, triazole)

where, for the synthesis of derivatives of the formula I, appropriate mercaptans or metal salts are reacted with a compound of the formula III

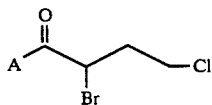

Substances of the structure II are potential highly potent pharmaceuticals with an antimycotic action and possible uses as crop protection agents and therefore are of great interest.

The compounds of the structure I used as starting materials have, however, unfortunately to date been preparable only via synthesis of appropriate mercaptans followed by reaction of the latter or their metal salts with compounds of the structure III. There was hence a need to acquire a considerably more straightforward access to I.

It has now been found, surprisingly, that the compounds of the formula I which are claimed as precursors in the abovementioned patent application can be obtained in a straightforward manner directly from an appropriate isothiuronium salt and a compound of the formula III under phase-transfer catalysis conditions.

Hence the invention relates to a process for the preparation of cyclopropane derivatives of the formula I,

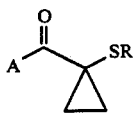

in which:

A = t-butyl, phenyl, biphenylyl, phenoxyphenyl, benzylphenyl, benzyloxyphenyl, phenylthiophenyl, phenylsulfinylphenyl, phenylsulfonylphenyl, naphthyl, 1,2,3,4-tetrahydronaphthyl, indanyl, fluoroenyl, thienyl, furyl, pyridyl, isoxazolyl, pyrazolyl, benzofuryl, benzothienyl, where the said ring systems are unsubstituted or substituted by 1–3 substituents which are identical or different and which are F, Cl, Br, I, $(C_1-C_8)$-alkyl, straight-chain or branched and unsubstituted or substituted with 1–9 F or Cl atoms, or $(C_3-C_{10})$-cycloalkyl (mono-, bi- or multicyclic, for example adamantyl, norbornyl, decahydronaphthalenyl), $(C_1-C_8)$-alkoxy, straight-chain or branched, and are unsubstituted or substituted by 1–9 F or Cl atoms, or $(C_3-C_8)$-cycloalkyl-$(C_1-C_4)$-alkyl, $(C_1-C_8)$-alkylthio, $(C_1-C_8)$-alkylsulfinyl and -sulfonyl, $NO_2$ or CN;

R = $(C_1-C_{12})$-alkyl (straight-chain or branched, unsubstituted or substituted by 1 to 3 F, Cl or Br atoms or $CH_3$ groups), $(C_2-C_{20})$-alkenyl (straight-chain or branched; mono- or polyunsaturated, in the form of the pure E or Z isomers or the E/Z diastereomer mixtures, unsubstituted or substituted by 1 to 3 F, Cl, or Br atoms or $CH_3O$ groups), $(C_2-C_{20})$-alkynyl (straight-chain or branched; unsubstituted or substituted by 1 to 3 F, Cl or Br atoms or $CH_3O$ groups), $(C_4-C_{20})$-alkenynyl (straight-chain or branched; mono- or polyunsaturated, in the form of the pure E or Z isomers or the E/Z diastereomer mixtures, unsubstituted or substituted by 1 to 3 F, Cl or Br atoms or $CH_3O$ groups), $(C_3-C_8)$-cycloalkyl, $(C_3-C_8)$-cycloalkyl-$(C_1-C_4)$-alkyl, phenyl, phenyl-$(C_1-C_4)$-alkyl, biphenylyl, phenoxyphenyl, phenylthiophenyl, phenyl-$(C_1-C_2)$-alkyl, naphthyl, biphenylyl-$(C_1-C_4)$-alkyl, phenylthiophenyl-$(C_1-C_4)$-alkyl, phenoxyphenyl-$(C_1-C_4)$-alkyl, naphthyl-$(C_1-C_4)$-alkyl, benzothiazol-2-yl, benzimidazol-2-yl, N-$(C_1-C_4)$-alkylbenzimidazol-2-yl, pyridyl, pyrid-2-yl-methyl, pyrid-3-yl-methyl, pyrid-4-yl-methyl, pyrimidin-2-yl, pyrimidin-2-yl-methyl, pyrimidin-4-yl-methyl, pyrimidin-5-yl-methyl, furfuryl, thien-2-yl, thien-3-yl, thien-2-yl-methyl, thien-3-yl-methyl, isoxazol-3-yl-methyl, isoxazol-4-yl-methyl, isoxazol-5-yl-methyl, oxazolyl-methyl, thiazol-2-yl-methyl, thiazol-5-yl-methyl, thiazol-5-yl-2-ethyl, $(C_2-C_3)$-alkyl-Y-aryl (with Y equal to S, O, SO or $SO_2$) and aryl equal to phenyl, benzyl, thien-2-yl-methyl, thien-3-yl-methyl), benzothiazol-2-yl-methyl, quinolinyl-methyl, pyridyl-phenyl-methyl, where the said ring systems are unsubstituted or substituted by 1, 2 or 3 substituents which are identical or different and each is F, Cl, Br, I, $CF_3$, $(C_1-C_8)$-alkyl, $(C_1-C_8)$-alkoxy, phenyl, and phenyl can be substituted by 1–3 substitutents F, Cl, Br, $CF_3$, $(C_1-C_8)$-alkyl, $(C_1-C_8)$-alkoxy.

The preparation of compounds I in which the substituents have the following meaning is preferred:

A = phenyl, biphenylyl, 1,2,3,4-tetrahydronaphthyl, thienyl, indanyl, in each case unsubstituted or substituted in the aromatic ring by one or two substituents which are identical or different and each is F, Cl, Br, $CF_3$, $(C_1-C_4)$-alkyl or $(C_1-C_4)$-alkoxy R = $(C_1-C_{15})$-alkyl, straight-chain or branched, $(C_2-C_{15})$-alkenyl, straight-chain or branched, mono- or polyunsaturated, phenyl, biphenylyl, phenoxyphenyl, phenylthiophenyl, benzyl, naphthyl, biphenylyl-$(C_1-C_2)$-alkyl, naphthyl-$(C_1-C_2)$- alkyl, benzothiazol-2-yl, benzimidazol-2-yl, furfuryl, thien-2-yl-methyl, thien-3-yl-methyl, isoxazol-3-yl-methyl, isoxazol-4-yl-methyl, isoxazol-5-yl-methyl, oxazolyl-methyl, pyrid-3-yl-methyl, pyrid-4-yl-methyl, ethyl-thioaryl with aryl equal to phenyl, benzyl, thien-2-yl-methyl, thien-3-yl-methyl, where the said ring systems are unsubstituted or substituted by 1, 2 or 3 substituents which are identical or different and each is F, Cl, Br, CF$_3$, methyl, methoxy groups.

Very particularly preferred is a process for the preparation of compounds I in which the substituents have the following meaning:

A = phenyl, thienyl, in each case unsubstituted or substituted by 1 or 2 F or Cl atoms, methyl, methoxy R = ($C_1$–$C_{12}$)-alkyl (straight-chain or branched), geranyl, neryl, phenyl, benzyl, naphthyl, thien-2-yl-methyl, thien-3-yl-methyl, isoxazol-4-yl-methyl, pyrid-3-yl-methyl, pyrid-4-yl-methyl, in each case unsubstituted or substituted once or twice by F, Cl, methyl, methoxy.

The ($C_1$–$C_{12}$)- or ($C_1$–$C_4$)-alkyl groups occurring as substituents or in connection with other substituents can be unbranched or branched and are, for example, the methyl, ethyl, propyl, 1-methylethyl, butyl, 2-methylpropyl, 1,1-dimethyl-ethyl-, pentyl-, hexyl-, heptyl-, octyl-, nonyl-, decyl-, undecyl-, dodecyl group;

the alkyl groups substituted by fluorine or chlorine can be, for example, the trifluoromethyl, trichloromethyl, 1,1,2,2,-tetrafluoroethyl or the nonafluorobutyl groups; the ($C_3$–$C_8$)-cycloalkyl groups can be the cyclopropyl, cyclobutyl, cyclopentyl, cyclohexyl, cycloheptyl or cyclooctyl groups;

the ($C_3$–$C_8$)-cycloalkyl-($C_1$–$C_4$)-alkyl groups can be, for example, the cyclopropylmethyl, cyclobutyl, cyclopentylmethyl, cyclohexylmethyl, cyclohexylethyl, cycloheptylmethyl or cyclooctylmethyl group.

The process according to the invention comprises reacting a compound of the formula III

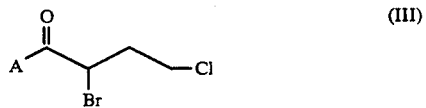

(III)

in which A has the abovementioned meaning, with a compound of the formula IV

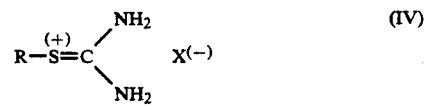

(IV)

to give compounds of the formula I where R has the abovementioned meaning, X is fluorine, chlorine, bromine or iodine and sulfate, and in the case of sulfate as counterion, mono- or dibasic salts are possible. In the case of monobasic salts, suitable as further cations are, for example, alkali metal or alkaline earth metal cations.

Compounds of the formula IV are prepared by processes known from the literature, advantageously by reacting an appropriate halide or sulfate of the formula

R—X        (V)

with thiourea with R and X as indicated above, in an inert solvent such as lower alcohols, such as methanol, ethanol or isopropanol, hydrocarbons such as benzene, toluene or halogenated hydrocarbons, such as dichloromethane, chloroform at temperatures from −10° to 150° C., preferably 10° to 80° C.

The compounds of the formula IV which are, in many cases, obtained by crystallization are reacted in the process according to the invention without further purification steps by stirring vigorously with compound III under phase-transfer catalysis conditions.

This reaction is advantageously carried out in a two-phase system, in which case, besides an aqueous strongly basic alkali metal or alkaline earth metal hydroxide solution with at least two equivalents of base, the organic phase is an inert solvent such as THF, diethyl ether, acetonitrile, a hydrocarbon such as pentane or hexane, a halogenated hydrocarbon such as dichloromethane, chloroform, tetrachloromethane, an aromatic hydrocarbon such as benzene, chlorobenzene, nitrobenzene, toluene or xylene or mixtures of these solvents.

Suitable phase-transfer catalysts are quaternary ammonium or phosphonium salts and crown ethers or polyethylene glycols. Examples of such compounds are compiled in the monograph by W. P. Weber and G. W. Gockel, Phase Transfer Catalysis in Organic Synthesis, Berlin, Springer Verlag, 1977. Particularly suitable for the process relating to the invention have proven to be tetra-n-butylammonium bromide and benzyltriethylammonium chloride.

The reaction relating to the invention is carried out in a temperature range from −10° to 150° C. under the conditions of a phase-transfer-catalyzed reaction. It is preferable to stir vigorously the reactants plus catalyst at temperatures from 10° to 80° C., in which case the start of the reaction is observed after a short time by an increase in the reaction temperature by 1° to 40° C. and a change in color of the reaction mixture.

The advantages have proven to be, besides a shortening of the reaction sequence and a saving of time, the avoidance of the mercaptan intermediate which has an unpleasant odor. In addition, it is possible by this process to increase the yield of the reaction in the case of some derivatives where the free mercaptide salt is prone to side reactions under the reaction conditions (see Example 3).

The examples which follow serve to illustrate the invention further.

EXAMPLE 1

Preparation of 1-(4-chorobenzoyl)-1-(4-pyridylmethylthio)cyclopropane 250 ml of toluene, 70 g of 50% strength aqueous NaOH solution, 16 g (67 mmol) of 4-pyridylmethylisothiuronium chloride and 1.5 g of tetrabutylammonium bromide are mixed together while stirring vigorously and cooling slightly, and subsequently 19.7 g (67 mmol) of 1-bromo-3-chloropropyl 4-chlorophenyl ketone are rapidly added. After ¼ hour the cooling is removed and the reaction mixture is then stirred at 20° C. for 2 hours.

For the working-up, 250 ml of diethyl ether and 100 ml of water are added, and the organic phase is separated off. The aqueous phase is extracted twice more with diethyl ether, and the combined organic phase is washed with water until neutral. The oily residue after drying with Na$_2$SO$_4$ and concentration in vacuo is chromatographed on silica gel (mobile phase $CH_2Cl_2$:ethyl acetate=1:1).

Yield: 19.77 g (oil, 97%; 65 mmol); colorless oil

EXAMPLE 2

Preparation of 1-(4-chlorobenzoyl)-1-(3,5-dimethyl-4-isoxazolylmethyl)cyclopropane 250 ml of toluene, 30 g of 50% strength aqueous NaOH, 1 g of triethylbenzylammonium chloride and 7.8 g (35 mmol) of 3,5-dimethyl-4-isoxazolylmethylisothiuroniumchlorideare mixed together by stirring at room temperature and, while stirring vigorously, 10.4 g (35 mmol) of 1-bromo-3-chloropropyl 4-chlorophenyl ketone are added. After a short time the reaction starts (reaction mixture becomes dark in color and the reaction temperature rises to 40° C.). After the reaction temperature has fallen back to room temperature (after about 4 hours) the mixture is poured into 500 ml of water and extracted with dichloromethane. The organic phase is washed until neutral, dried over $Na_2SO_4$ and concentrated in vacuo, and the residue is chromatographed on silica gel (mobile phase dichloromethane).

Yield: 9.39 g (29.1 mmol; 83% of theory); colorless oil

EXAMPLE 3

Preparation of 1-(4-chlorobenzoyl)-1-(4-chlorophenylthioethylthio)-cyclopropane 12.5 g (44 mmol) of 4-chlorophenylthioethylisothiuronium chloride and 13 g (44 mmol) of 1-bromo-3-chloropropyl 4-chlorophenyl ketone are added successively while cooling in ice to 250 ml of toluene, 50 g of 50% strength aqueous KOH and 1.5 g of tetra-n-butylammonium bromide. After removal of the cooling, the reaction started and the reaction temperature jumped to 42° C. After the reaction is complete—detectable by the fall in the reaction temperature to room temperature—the mixture is poured into water and extracted with dichloromethane, and the organic phase is dried over $Na_2SO_4$ and concentrated in vacuo. The remaining oil is chromatographed on silica gel (mobile phase dichloromethane: ethyl acetate=1:1).

Yield: 14.5 g=38 mmol; 86% of theory; colorless crystals of melting point 63°-66° C.

The compounds listed in the following table were prepared in an analogous manner. The compounds are generally oils and were characterized by $^1H$—NMR spectroscopy and/or elemental analysis. Further characterization was carried out by converting the compounds into the corresponding cyclopropylazoles of the formula II with triazole or imidazole residue, whose synthesis and characterization is described in Patent EP-A 0 237 917.

TABLE

Prepared compounds of the structural formula I

| No. | A | R | Catalyst | Yield |
|---|---|---|---|---|
| 4 | $C_6H_4$—4—Cl | $CH_2$-pyrid-3-yl | $Bu_4NBr$ | 91% |
| 5 | $C_6H_4$—4—Cl | $CH_2$—CH=C(CH$_3$)$_2$ | $Bu_4NBr$ | 50% |
| 6 | $C_6H_4$—4—Cl | $CH_2$—2,3-Cl$_2$-thien-5-yl | $Bu_4NBr$ | 58% |
| 7 | $C_6H_4$—4—Cl | $CH_2$—3-Cl$_2$-thien-2-yl | $BzEt_3NCl$ | 73% |
| 8 | $C_6H_4$—4—Cl | $CH_2$—5-Cl$_2$-thien-2-yl | $Bu_4NBr$ | 63% |
| 9 | $C_6H_4$—4—Cl | E-3,7-Me$_2$-2,6-octadien-1-yl | $Bu_4NBr$ | 57% |
| 10 | $C_6H_4$—4—Cl | $CH_2$-thienyl | $Bu_4NBr$ | 73% |
| 11 | $C_6H_4$—4—Cl | $CH_2$—5-Br-thien-2-yl | $Bu_4NBr$ | 56% |
| 12 | $C_6H_4$—4—Cl | $CH_2$—2,5-Cl$_2$-thien-3-yl | $Bu_4NBr$ | 85% |
| 13 | $C_6H_4$—4—Cl | $CH_2$—CH$_2$-S-benzyl | $Bu_4NBr$ | 40% |
| 14 | $C_6H_4$—4—Cl | $CH_2$-thien-3-yl | $BzEt_3NCl$ | 40% |
| 15 | $C_6H_4$—4—Cl | $CH_2$—CH$_2$-4-Me-thiazol-5-yl | $Bu_4NBr$ | 30% |
| 16 | $C_6H_4$—4—Cl | $CH_2$-pyrid-2-yl | $Bu_4NBr$ | 95% |
| 17 | $C_6H_4$—4—F | $CH_2$—Cl$_2$-thien-2-yl | $Bu_4NBr$ | 70% |
| 18 | $C_6H_4$—4—F | $CH_2$—2,5-Cl$_2$-thien-3-yl | $Bu_4NBr$ | 74% |
| 19 | $C_6H_4$—4—F | $CH_2$—CH$_2$—S—CH$_2$—C$_6$H$_5$ | $Bu_4NBr$ | 61% |
| 20 | $C_6H_4$—4—F | $CH_2$-pyrid-4-yl | $BzEt_3NCl$ | 85% |
| 21 | $C_6H_4$—4—Cl | $CH_2$-5-Br-furan-2-yl | $Bu_4NBr$ | 41% |
| 22 | $C_6H_4$—4—Cl | Z-3,7-CH$_3$-2,6-octadien-1-yl | $Bu_4NBr$ | 52% |
| 23 | $C_6H_4$—4—F | Z-3,7-CH$_3$-2,6-octadien-1-yl | $Bu_4NBr$ | 53% |
| 24 | $C_6H_4$—4—F | $CH_2$-thien-2-yl | $Bu_4NBr$ | 96% |
| 25 | Indan-2-yl | $CH_2$-thie-2-yl | $BzEt_3NCl$ | 86% |
| 26 | Tetralin-2-yl | $CH_2$-thien-2-yl | $Bu_4NBr$ | 87% |
| 28 | $C_6H_4$—4—t—$C_4H_9$ | $CH_2$-thien-2-yl | $Bu_4NBr$ | 75% |
| 29 | $C_6H_4$—4—CH$_3$ | $CH_2$-3-Cl-thien-2-yl | $BzEt_3NCl$ | 90% |
| 30 | Indan-2-yl | $CH_2$-3-Cl-thien-2-yl | $Bu_4NRr$ | 90% |
| 31 | Indan-2-yl | $CH_2$-2,5-Cl$_2$-thien-3-yl | $Bu_4NBr$ | 95% |
| 31 | $C_6H_4$—4—F | $CH_2$-3-Cl-thien-2-yl | $BzEt_3NCl$ | 35% |
| 32 | $C_6H_4$—4—Cl | $CH_2$—CH$_2$-S-(4-Cl-benzyl) | $Bu_4NBr$ | 35% |
| 33 | $C_6H_4$—4—OCH$_3$ | $CH_2$-pyrid-4-yl | $Bu_4NBr$ | 87% |
| 34 | $C_6H_4$—4—Cl | $CH_2$-quinolin 3-yl | $Bu_4NBr$ | 59% |
| 35 | $C_6H_4$—4—F | $CH_2$—CH$_2$-S-(4-Cl-benzyl) | $Bu_4NBr$ | 38% |
| 36 | $C_6H_4$—4—F | E-3,7-Me$_2$-2,6-octadien-1-yl | $Bu_4NBr$ | 83% |
| 37 | $C_6H_4$—4—Cl | $CH_2$-2-Br-pyrid 4-yl | $Bu_4NBr$ | 48% |
| 38 | $C_6H_4$—4—Cl | $CH_2$-C$_6$H$_4$-pyrid-2-yl | $Bu_4NBr$ | 58% |
| 39 | $C_6H_3$—2,4—F$_2$ | $CH_2$-pyrid-3-yl | $Bu_4NBr$ | 51% |
| 40 | $C_6H_4$—4—Cl | $CH_2$-(3-CH$_3$-isoxazol-5-yl) | $Bu_4NBr$ | 96% |
| 41 | $C_6H_4$—4—Cl | $CH_2$-(5-pyrid-2-yl)-thien-2-yl | $Bu_4NBr$ | 48% |
| 42 | $C_6H_3$—2,4—F$_2$ | $CH_2$-pyrid-4-yl | $Bu_4NBr$ | 59% |
| 43 | $C_6H_3$—2,4—F$_2$ | $CH_3$ | $Bu_4NBr$ | 40% |
| 44 | $C_6H_4$—4—Cl | $CH_2$-(2-phenyl)-pyrimidin-5-yl | $Bu_4NBr$ | 81% |
| 45 | $C_6H_4$—2—Cl—4—F | $CH_2$-pyrid-4-yl | $Bu_4NBr$ | 90% |

TABLE-continued

Prepared compounds of the structural formula I

| No. | A | R | Catalyst | Yield |
|---|---|---|---|---|
| 46 | $C_6H_4$—4—Cl | $CH_2$-(3,5-$(CH_3)_2$-isoxazol-4-yl) | $Bu_4NBr$ | 90% |
| 47 | $C_6H_4$—4—Cl | $CH_2$-(5-($CH_3$-isoxazol-3-yl)) | $Bu_4NBr$ | 89% |
| 48 | $C_6H_4$—4—Cl | $CH_2$(3-ethyl-5-methyl-isoxazol-4-yl) | $Bu_4NBr$ | 82% |
| 49 | $C_6H_4$—4—Cl | $CH_2$(5-methyl-3-(3-chlorophenyl)-isoxazol-4-yl) | $Bu_4NBr$ | 67% |
| 50 | $C_6H_4$—4—Cl | $CH_2$-(3-heptyl-isoxazol-5-yl) | $Bu_4NBr$ | 73% |
| 51 | $C_6H_4$-4-Cyclohexyl | $CH_2$-3,4-$(CH_3)_2$-$C_6H_3$ | $Bu_4NBr$ | 48% |
| 52 | $C_6H_4$-4-Cyclohexyl | $CH_2$-pyrid-4-yl | $Bu_4NBr$ | 64% |
| 53 | $C_6H_4$-4-Cyclohexyl | $CH_2$-(4-$CF_3$—$C_6H_4$) | $Bu_4NBr$ | 66% |
| 54 | $C_6H_4$-4-n-$C_7H_{15}$ | $CH_2$-(3-$CF_3$—$C_6H_4$) | $Bu_4NBr$ | 91% |
| 55 | $C_6H_4$-4-$CH_3$ | $CH_2$-(3-$CF_3$—$C_6H_4$) | $Bu_4NBr$ | 60% |
| 56 | $C_6H_4$-4-t-butyl | $CH_2$-(3-$CF_3$—$C_6H_4$) | $Bu_4NBr$ | 92% |
| 57 | $C_6H_4$-4-Cyclohexyl | $CH_2$-(3-$CF_3$—$C_6H_4$) | $Bu_4NBr$ | 62% |
| 58 | $C_6H_4$-4-Cl | $CH_2$—$C_6H_4$-4-t-butyl | $Bu_4NBr$ | 56% |
| 59 | $C_6H_4$-4-t-butyl | $CH_2$-(3,4-$(CH_3)_2$-isoxazol-4-yl) | $Bu_4NBr$ | 92% |
| 60 | $C_6H_4$-4-Cyclohexyl | $CH_2$—$C_6H_4$-4-t-butyl | $Bu_4NBr$ | 60% |
| 61 | $C_6H_4$-4-butyl | $CH_2$—$C_6H_4$-4-t-butyl | $Bu_4NBr$ | 75% |
| 62 | $C_6H_4$—4—Cl | $CH_2$—$C_6H_4$-3-$CF_3$ | $Bu_4NBr$ | 79% |
| 63 | $C_6H_4$-4-adamant-2-yl | $CH_2$-(3-$CF_3$—$C_6H_4$) | $Bu_4NBr$ | 77% |
| 64 | $C_6H_4$-4-adamant-2-yl | $CH_2$-(4-Cl—$C_6H_4$) | $Bu_4NBr$ | 56% |

With the exception of compound 43, all the compounds in Table 1 were synthesized from the corresponding isothiuronium chlorides or bromides. The corresponding sulfate was used to prepare 43.

We claim:

1. A process for the preparation of cyclopropane derivatives of the formula I

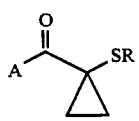

(I)

in which:

A = phenyl, biphenylyl, phenoxyphenyl, benzylphenyl, benzyloxyphenyl, phenylthiophenyl, phenylsulfinylphenyl, phenylsulfonylphenyl, naphthyl, 1,2,3,4-tetrahydronaphthyl, indanyl, fluoroenyl, where the said ring systems are unsubstituted or substituted by 1-3 substituents which are identical or different and which are F, Cl, Br, I, ($C_1$-$C_8$)-alkyl, straight-chain or branched and unsubstituted or substituted with 1-9 F or Cl atoms, or ($C_3$-$C_{10}$)-cycloalkyl (mono-, bi- or multicyclic), ($C_1$-$C_8$)-alkoxy, straight-chain or branched, and are unsubstituted or substituted by 1-9 F or Cl atoms, or ($C_3$-$C_8$)-cycloalkyl-($C_1$-$C_4$)-alkyl, ($C_1$-$C_8$)-alkylthio, ($C_1$-$C_8$)-alkylsulfinyl and -sulfonyl, $NO_2$ or CN;

R = ($C_1$-$C_{12}$)-alkyl (straight-chain or branched, unsubstituted or substituted by 1 to 3 F, Cl or Br atoms or $CH_3$ groups), ($C_2$-$C_{20}$)-alkenyl (straight-chain or branched; mono- or polyunsaturated, in the form of the pure E or Z isomers or the E/Z diastereomer mixtures, unsubstituted or substituted by 1 to 3 F, Cl, or Br atoms or $CH_3O$ groups), ($C_2$-$C_{20}$)-alkynyl (straight-chain or branched; unsubstituted or substituted by 1 to 3 F, Cl or Br atoms or $CH_3O$ groups), ($C_4$-$C_{20}$)-alkenynyl (straight-chain or branched; mono- or polyunsaturated, in the form of the pure E or Z isomers or the E/Z diastereomer mixtures, unsubstituted or substituted by 1 to 3 F, Cl or Br atom or $CH_3O$ groups), ($C_3$-$C_8$)-cycloalkyl, ($C_3$-$C_8$)-cycloalkyl-($C_1$-$C_4$)-alkyl, phenyl, phenyl-($C_1$-$C_4$)-alkyl, biphenylyl, phenoxyphenyl, phenylthiophenyl, phenyl-($C_1$-$C_2$)-alkyl, naphthyl, biphenylyl-($C_1$-$C_4$)-alkyl, phenylthiophenyl-($C_1$-$C_4$)-alkyl, phenoxyphenyl-($C_1$-$C_4$)-alkyl, naphthyl-($C_1$-$C_4$)-alkyl, benzothiazol-2-yl, benzimidazol-2-yl, N-($C_1$-$C_4$)-alkylbenzimidazol-2-yl-, pyridyl, pyrid-2-yl-methyl, pyrid-3-yl-methyl, pyrid-4-yl-methyl, pyrimidin-2-yl, pyrimidin-2-yl-methyl, pyrimidin-4-yl-methyl, pyrimidin-5-yl-methyl, furfuryl, thien-2-yl, thien-3-yl, thien-2-yl-methyl, thien-3-yl-methyl, isoxazol-3-yl-methyl, isoxazol-4-yl-methyl, isoxazol-5-yl-methyl, oxazolyl-methyl, thiazol-2-yl-methyl, thiazol-5-yl-methyl, thiazol-5-yl-2-ethyl, ($C_2$-$C_3$)-alkyl-Y-aryl (with Y equal to S, O, SO or $SO_2$) and aryl equal to phenyl, benzyl, thien-2-yl-methyl, thien-3-yl-methyl), benzothiazol-2-yl-methyl, quinolinyl-methyl, pyridyl-phenyl-methyl, where the said ring systems are unsubstituted or substituted by 1, 2 or 3 substituents which are identical or different and each is F, Cl, Br, I, $CF_3$, ($C_1$-$C_8$)-alkyl, ($C_1$-$C_8$)-alkoxy, phenyl, and phenyl can be substituted by 1-3 substituents F, Cl, Br, $CF_3$, ($C_1$-$C_8$)-alkyl, ($C_1$-$C_8$)-alkoxy, which comprises reacting a compound of the formula III

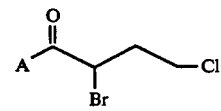

(III)

in which A has the abovementioned meaning, with a compound of the formula IV

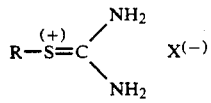

to give compounds of the formula I where R has the abovementioned meaning, X is fluorine, chlorine, bromine or iodine and sulfate.

2. The process as claimed in claim 1, in which are employed compounds III in which the substituents have the following meaning:

A = phenyl, biphenylyl, 1,2,3,4-tetrahydronaphthyl, indanyl, in each case unsubstituted or substituted in the aromatic ring by one or two substituents which are identical or different and each is F, Cl, Br, $CF_3$, $(C_1-C_4)$-alkyl or $(C_1-C_4)$-alkoxy R = $(C_1-C_{15})$-alkyl, straight-chain or branched, $(C_2-C_{15})$-alkenyl, straight-chain or branched, mono- or polyunsaturated, phenyl, biphenylyl, phenoxyphenyl, phenylthiophenyl, benzyl, naphthyl, biphenylyl-$(C_1-C_2)$-alkyl, naphthyl-$(C_1-C_2)$-alkyl, benzothiazol-2-yl, benzimidazol-2-yl, furfuryl, thien-2-yl-methyl, thien-3-yl-methyl, isoxazol-3-yl-methyl, isoxazol-4-yl-methyl, isoxazol-5-yl-methyl, oxazolyl-methyl, pyrid-3-yl-methyl, pyrid-4-yl-methyl, ethyl-thioaryl with aryl equal to phenyl, benzyl, thien-2-yl-methyl, thien-3-yl-methyl, where the said ring systems are unsubstituted or substituted by 1, 2 or 3 substituents which are identical or different and each is F, Cl, Br, $CF_3$, methyl, methoxy groups.

3. The process as claimed in claim 1, in which are employed compounds III in which A is phenyl, in each case unsubstituted or substituted by 1 or 2 F or Cl atoms, methyl, methoxy and R is $(C_1-C_{12})$-alkyl (straight-chain or branched), geranyl, neryl, phenyl, benzyl, naphthl, thien-2-yl-methyl, thien-3-yl-methyl, isoxazol-4-yl-methyl, pyrid-3-yl-methyl, pyrid-4-yl-methyl, in each case unsubstituted or substituted once or twice by F, Cl, methyl, methoxy.

* * * * *

UNITED STATES PATENT AND TRADEMARK OFFICE
CERTIFICATE OF CORRECTION

PATENT NO. : 5,189,165
DATED : February 23, 1993
INVENTOR(S) : Gerhard Burdinski et al.

It is certified that error appears in the above-identified patent and that said Letters Patent is hereby corrected as shown below:

Claim 1, column 8, line 33, change "atom" to --atoms--.

Claim 1, column 8, line 41, change "2-yl-," to --2-yl,--.

Claim 3, column 10, line 17, change "naphthl" to --naphthyl--.

Signed and Sealed this

Fourteenth Day of December, 1993

Attest:

BRUCE LEHMAN

Attesting Officer          Commissioner of Patents and Trademarks